United States Patent [19]

Elongo

[11] Patent Number: 4,883,901

[45] Date of Patent: Nov. 28, 1989

[54] SYNTHESIS OF 2-(4-AMINOPHENOXY)ALKANOIC ACIDS AND ESTERS AND THEIR DERIVATIVES

[75] Inventor: Varadaraj Elongo, Corpus Christi, Tex.

[73] Assignee: Hoechst Celanese Corporation, Sommerville, N.J.

[21] Appl. No.: 170,712

[22] Filed: Mar. 21, 1988

[51] Int. Cl.$^4$ ............................................ C07C 101/72
[52] U.S. Cl. ...................... 560/45; 260/404; 260/404.5; 558/47; 558/48; 558/49; 558/50; 558/413; 558/414; 558/415; 562/430; 562/435; 562/437; 562/440; 562/455
[58] Field of Search ...................... 560/45, 34, 35, 53, 560/21, 22, 12, 13; 260/404, 404.5; 558/47, 49, 50, 414, 415, 48, 413; 562/435, 437, 455, 430, 440

[56] References Cited

U.S. PATENT DOCUMENTS

| | | | |
|---|---|---|---|
| 3,081,302 | 3/1963 | Shapiro et al. | 560/45 |
| 3,278,524 | 10/1966 | Johnson et al. | 260/239.1 |
| 4,358,307 | 11/1982 | Serban et al. | 71/92 |
| 4,439,226 | 3/1984 | Pilgram | 71/92 |

FOREIGN PATENT DOCUMENTS

916242 1/1963 United Kingdom .

OTHER PUBLICATIONS

Chemical Abstracts, vol. 59, No. 5080, Substituted Propionic Acids as Anti-Inflammatory Agents, (British Patent) 916,242, (1963).

Journal of Organic Chemistry, Smiles Rearrangement on Borohydride Reduction of a Nitrophenoxy Ester, M. Harefenist, et al., vol. 36, No. 9, (1971).

*Primary Examiner*—Bruce Gray
*Attorney, Agent, or Firm*—Donald R. Cassady

[57] ABSTRACT

A method for synthesizing 2-(4-amidophenoxy)alkanoic acids and esters and 2-(4-aminophenoxy)alkanoic acids and esters by reacting a hydroxyaromatic ketone derivative with a 2-substituted alkanoic acid or ester under basic conditions and thereafter reacting with a hydroxylamine derivative and conducting a Beckmann Rearrangement in the presence of a catalyst with subsequent solvolysis.

36 Claims, No Drawings

SYNTHESIS OF 2-(4-AMINOPHENOXY)ALKANOIC ACIDS AND ESTERS AND THEIR DERIVATIVES

BACKGROUND OF THE INVENTION

The present invention relates to a method for the synthesis of 2-(4-amidophenoxy)alkanoic acids and esters and 2-(4-aminophenoxy)alkanoic acids and esters. Such compounds are useful in the production of pharmaceuticals and herbicides. See, for example, U.S. Pat. Nos. 3,278,524; 3,081,302; 4,439,226, 4,358,307 and British Pat. No. 916,242.

U.S. Pat. No. 3,278,524, teaches the preparation of 2-(4-acetaminophenoxy)propanoic acid by reacting 2-halo propionic acids with 4-acetaminophenol under basic conditions. Similarly, U.S. Pat. No. 3,081,302, teaches the condensation of 4-acetaminophenol with 2-halo-alkanoic acid esters in the presence of a base to give 2-(4-acetaminophenoxy)alkanoic acid esters. Such a process is economically disadvantageous, and hence the poor yield.

U.S. Pat. No. 4,439,226, and Journal of Organic Chemistry (Vol.36, pages 1171–1178, 1971) describe the synthesis of 2-(4-aminophenoxy)propanoic acid esters via sequential condensation of 4-nitrophenol with 2-halopropanoic acid esters in the presence of a base and reduction. These processes proceeds with moderate yields and hence they are not economically advantageous. Furthermore, salts of nitrophenols can explode if allowed to become dry, especially if heated.

The prior art does not disclose the conversion of acylaromatic compounds to the corresponding acetamide or aminoaromatic compounds. Such a process would be economically desired as it overcomes the deficiencies mentioned heretofore.

The present invention provides a procedure for producing intermediates which are 2-(4-aminophenoxy)alkanoic acids or esters, preferably, 2-(4-acetaminophenoxy)alkanoic acids or esters as well as 2-(4-aminophenoxy)alkanoic acids or esters.

SUMMARY OF THE INVENTION

The invention provides a method for synthesizing 2-(4-amidophenoxy)alkanoic acids or esters as well as 2-(4-aminophenoxy)alkanoic acids or esters which comprises reacting a hydroxyaromatic ketone or benzaldehyde derivative of the formula

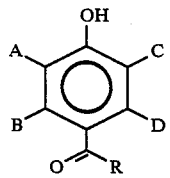
(I)

or a salt thereof; with a substituted acid or ester of the formula

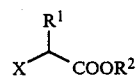

under basic conditions to thereby form a 2-(4-acylphenoxy)alkanoic acid or ester derivative (II) of the formula

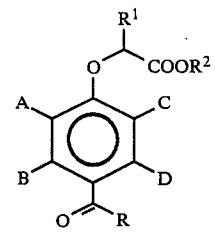
(II)

This 2-(b 4-acylphenoxy)alkanoic acid or ester (II) is then reacted with an a hydroxylamine derivative to form a 2-(4-acyliminophenoxy)alkanoic acid or ester (III) of the formula

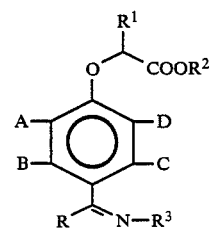
(III)

which is then subjected to a Beckmann Rearrangement in the presence of a catalyst to obtain a 2-(4-amidophenoxy)alkanoic acid or ester (IV) of the formula

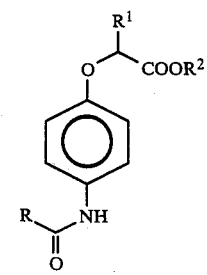
(IV)

In order to obtain 2-(4-aminophenoxy)aklanoic acid or ester, the aforesaid 2-(4-amidophenoxy)alkanoic acid or ester (V) is hydrolyzed with $R^4OH/H^+$ to obtain a compound formula:

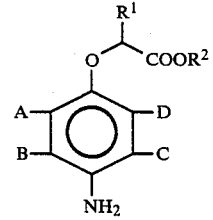
(V)

In the above formulae: R is H, $C_1$ to $C_{18}$ alkyl or $C_6$ to $C_{18}$ aryl, preferably H, or $C_1$ to $C_4$ alkyl, most preferably H or methyl; and wherein $R^1$ is H, phenyl or $C_1$ to $C_{18}$ alkyl, preferably H, or $C_1$ to $C_4$ alkyl, and most preferably H or methyl; and where $R^2$ and $R^4$ are independently $HC_1$ to $C_{18}$ alkyl, preferably $C_1$ to $C_4$ alkyl or aryl such as phenyl or naphthyl which may be substituted or unsubstituted; $R^3$ is OH, $O-SO_3H$; and A, B, C and D are independently H, S, O, N, X, $CF_3$, $NO_2$, CN, $C_1$ to $C_4$ alkyl or alkoxy, or $C_6$ to $C_{10}$ aryl, protected using methods well-known to those skilled in the art so to avoid reaction of said substituents under the conditions of the process, i.e., alkylation, oxidation, solvolysis; and X is F, Cl, Br, I or a sulfonic ester. The compounds of the formulae II, III, IV and V possess an asymmetric carbon center and can therefore occur as pure enantiomers (optically active) or racemic as mixtures of enantiomers.

DETAILED DESCRIPTION OF THE PREFERRED EMBODIMENT

In the production of the alkanoic acids and esters of this invention, one preferably begins with a hydroxyaromatic ketone and reacts it with one of the aforesaid substituted acids or esters under basic conditions. This reaction product is then reacted with a hydroxylamine derivative and then subjected to a Beckmann rearrangement in the presence of a catalyst. The resulting product is the desired 2-(amidophenoxy)alkanoic acid or ester. This resulting product may then hydrolyzed or alcoholized to obtain the desired 2-(4-aminophenoxyalkanoic acid or ester. The reaction sequence may be generalized as:

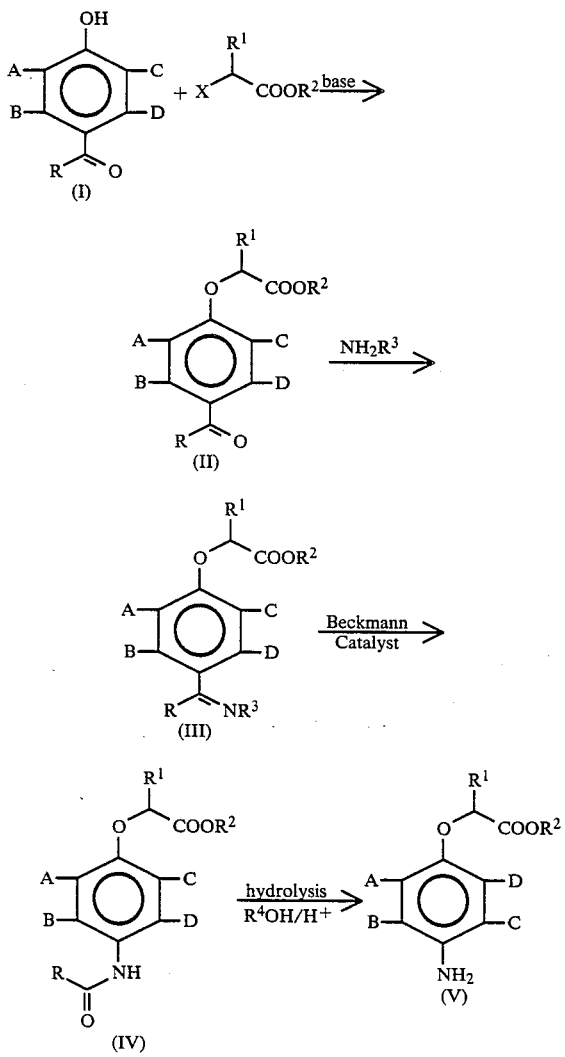

The preferred embodiment will now be set forth in further detail, and the skilled artisan can well obtain the analogous compounds. An important feature of this invention is to begin the synthesis with a hydroxyaromatic ketone (I) or benzaldehyde derivative which is preferably a 4-hydroxyacetophenone compound. The most preferred compound is 4-hydroxyacetophenone, as well as its sodium and potassium salts. The hydroxyaromatic ketone is then reacted with one of the aforesaid X-substituted acids or esters which may be optically active or racemic. Preferred esters are halogen substituted propanoates such as methyl 2-chloropropanoate, methyl 2-bromopropanoate, and ethyl 2-chloropropanoate, alkyl 2-[(methylsulfonyl)oxy]propanoate and alkyl 2-[(toluylsulfonyl)oxy]propanoate. This reaction proceeds by the Williamson's ether synthesis which is also well known to the skilled artisan. The reaction may take place by refluxing the hydroxyaromatic ketone with the ester in a solvent such as dimethylformamide under basic conditions. The basic conditions may be provided either by use of a base such as an alkali metal or alkaline earth metal hydroxide or carbonate, amines or a hydride such as sodium hydride. Alternatively, within the meaning of this invention, the basic media may be provided by using one of the aforesaid salt forms of the hydroxyaromatic ketones, such as 4-hydroxyacetophenone sodium or potassium salt. Alternative solvents for the refluxing reaction non-exclusively include polar protic solvents, e.g., water or alcohol; or polar aprotic solvents, e.g., ketones, ethers, nitriles, and sulfoxides. The reaction may take place at a temperature of from about 0.1 to about 100 hours, or more preferably from about 1 to about 50 hours at a temperature of from about 0° C. to about 200° C. or more preferably from about 25° C. to about 200° C. The reaction product of this juncture is a 2-(4-acylphenoxy)alkanoic ester derivative. In the preferred embodiment the forgoing reactants are 4-hydroxyacetophenone potassium salt and methyl 2-bromopropionate with refluxing in dimethylformamide. Therefore the preferred compound produced is methyl 2-(4-acetylphenoxy)propionate. In the alternative, instead of the aforesaid substituted ester, one could use a substituted acid of the formula:

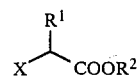

wherein $R^2$ is as described before. This component is then reacted with an amine such as $H_2N-R^3$ wherein $R^3$ is OH, $O-SO_3H$, where R is as described before. In the most preferred embodiment, hydroxylamine is employed. Other preferred amines non-exclusively include hydrazoic acid and hydroxylamine-O-sulfuric acid. The reaction product at this point is a 2-(4-acyliminophenoxy)alkanoic acid or ester.

This component is then subjected to a Beckmann Rearrangement process which is well known to the skilled artisan per se. This causes a shift of the $R^3$ group from its carbon bond to a bond with the nitrogen. The rearrangement is conducted with any commonly employed Beckmann catalyst. In the preferred embodiment an acid catalyst is used in a suitable solvent. The most preferred acid is sulfuric acid. Others non-exclusively include, thionyl chloride and polyphosphoric acid. One preferred solvent is acetic acid. Alternative solvents non-exclusively include carboxylic acids, esters, nitriles and ethers. The reaction may take place at a temperature of from about 0.1 to about 12 hours, or more preferably from about 0.5 to about 6 hours at a temperature of from about 40° C. to about 130° C. or more preferably from about 80° C. to about 120° C. The reaction product of this juncture is a 2-(4-acetamidophenoxy)alkanoic acid or ester which in the preferred embodiment is a 2-(4-acetamidophenoxy)propanoic acid or ester. This latter component may then be hydrolyzed or alcoholyzed. The alcoholysis may be conducted by contacting with alcohols under acidic conditions and elevated temperatures for a period of time sufficient to permit the reaction to approach completion. The amount of alcohol used may be, for example, about 0.5 to about 1,000 mol equivalents, preferably about 1 to about 100 mol equivalents based on the ester being alcoholized. The acids which may be employed for this purpose are organic acids such as methanesulfonic acid, para-toluenesulfonic acid, mineral acids such as sulfuric, hydrochloric and phosphoric acids, and acidic ion exchange resins. In some instances, it may be desirable to employ a combination of alcohol and water to achieve a measure of solvolysis. The hydrolysis may be conducted by refluxing with alcohols, ion exchange resins and/or acids such as hydrochloric acid and sulfuric acid.

Hydrolysis may take place at from about 0.1 to about 10 hours, or more preferably from about 0.5 to about 4 hours at a temperature of from about 20° C. to about 200° C., or more preferably from about 60° C. to about 140° C. The reaction is conducted with an anticipated conversion of from about 90% to about 99% with a selectivity of from about 90% to about 98%. The solvolysis product is a 2-(4-aminophenoxy)alkanoic acid or ester which in the preferred embodiment is a 2-(4-aminophenoxy)propanoic acid or ester. The alcoholysis process of this invention provides for the recovery of the amino product in relatively higher yields. The product may be recovered by conventional purification methods usually involving a combination of crystallization, filtration, washing and distillation in any order deemed advantageous for the system at hand.

The following non-limiting examples serve to illustrate the invention.

EXAMPLE 1

To a solution of 4-hydroxyacetophenone potassium salt (8.8 g, 500 mmol) in methanol (50 mL) is added methyl 2-bromopropanoate (11.08, 65.0 mmol) dropwise over 30 minutes under nitrogen. The mixture is refluxed under nitrogen for 24 hours during which KBr is accumulated. The reaction is monitored by thin layer chromatography using 100% ethyl acetate. The reaction is cooled to room temperature and the KBr is filtered out. Ethyl acetate (50 mL) is added to give a turbid solution which is refiltered. The reaction product is analyzed by GLC and found to yield methyl 2-(4-acetylphenoxy)propanoate (13.2 g). (m.p. 54.8° C.); IR (KBr) 1757.7 (vs), 1666.8 (vs); $^1$H NMR (CDCl$_3$) delta 1.54 (d, J=6.8 Hz, 3H), 2.42 (s, 3H), 3.64 (s, 3H), 4.76 (q, J=6.8 Hz, 1H), 6.79 and 7.80 (dd, J=8.0 Hz, 4H).

EXAMPLE 2

To a solution of the potassium salt of 4-hydroxyacetophenone (25.0 g, 0.14 mol) in dimethylformamide (DMF) (100 mL) is added methyl 2-chloropropanoate (24.5 g, 0.20 mol) over 30 minutes and stirred as 85°–90° C. for 3 hours under nitrogen. The reaction is filtered to remove KCl and the filtrate is concentrated under reduced pressure to remove DMF and the product analyzed by GLC. The product is dissolved in ethyl acetate (300 mL) and extracted with 2N NaOH (2×100 mL) and water (100 mL). The organic phase is dried and concentrated to give pure methyl 2-(4-acetylphenoxy)propanoate (25 g) (yield 64%).

EXAMPLE 3

To a solution of the potassium salt of 4-hydroxyacetophenone (25.0 g, 0.14 mol) in DMF (100 mL) is added ethyl 2-chloropropanoate (27.3 g, 0.20 mol) over 30 minutes and stirred at 85°–90° C. for 3 hours under nitrogen. The reaction is filtered to remove KCl and the filtrate is concentrated under reduced pressure to remove DMF and the product is analyzed by GLC. The product is dissolved in ethyl acetate (300 mL) and extracted with 2N NaOH (2×100 mL) and water (100 mL). The organic phase is dried and concentrated to give pure ethyl 2-(4-acetylphenoxy)propanoate (30 g) (yield 75%); m.p. 49.6° C.; IR (KBr) 1747.7 (vs), 1669.8 (vs); $^1$H NMR (CDCl$_3$) delta 1.18 (t, J=7.2 Hz, 3H), 1.58 (d, J=6.8 Hz, 3H), 2.46 (s, 3H), 4.15 (q, J=7.2, 2H), 4.77 (q, J32 6.8, 1H), 6.83 and 7.84 (dd, J=9.0 Hz, 4H).

EXAMPLE 4

A solution of the potassium salt of 4-hydroxyacetophenone (17.6 g, 0.1 mol) in DMF (50 mL) is added to a solution of ethyl L-2-[methylsulfonyl)oxy]propanoate (21.5 g, 0.11 mol) in DMF (40 mL) over 15 minutes at 80° C. and stirred at 80° C. for 2 hours. To the reaction is added ethyl acetate (100 mL) and filtered. The filtrate is concentrated under reduced pressure whereupon the product is analyzed by GLC. The product is dissolved in ethyl acetate (250 mL) and extracted with saturated sodium bicarbonate solution (2×100 mL) and water (2×60 mL). The organic phase is dried and concentrated to give ethyl D-2-(4-acetylphenoxy)propanoate (20.2 g).

EXAMPLE 5

Potassium hydroxide (17.0 g, 0.3 mol) is added to water (50 mL) and allowed to dissolve. The solution is added to 4-hydroxyacetophenone (13.6 g, 0.1 mol) to produce the potassium salt of 4-hydroxyacetophenone. 2-Bromopropanoic acid (17.0 g, 0.11 mol) is added to the potassium salt of 4-hydroxyacetophenone to give a yellow suspension. The solution is heated to reflux (102° C.) during which a yellow solution results. The solution is refluxed for 24 hours and cooled to room temperature. The pH is adjusted to 6–7 and extracted with ethyl acetate (3×100 mL) and the solution is concentrated under reduced pressure. The aqueous layer is acidified to pH 2 and extracted with ethyl acetate (3×150 mL). The solution is concentrated to give 7.0 g of a brown liquid which is 2-(4-acetylphenoxy)propanoic acid at a yield of 34%.

EXAMPLE 6

To a solution of the potassium salt of 4-hydroxyacetophenone (8.8 g, 0.05 mol) in dimethylformamide (25 mL) is added methyl 2-bromopropanoate (10.2 g, 0.06 mol) over 30 minutes and stirred at 80°–90° C. for 4 hours under nitrogen. The reaction is cooled to room temperature and methylene chloride (75 mL) and water (75 mL) are added. The organic phase is separated, washed with water (100 mL), dried and concentrated to give methyl 2-(4-acetylphenoxy)propanoate (8.5 g) (yield 76%). Methyl 2-(4-acetylphenoxy)propanoate (7.0 g, 31.5 mmol) is combined with 2N NaOH (20 mL) and refluxed overnight. Water (30 mL) is added to the reaction which is then washed with methylene chloride (50 mL). It is then acidified to pH=1 with concentrated hydrochloric acid and extracted with ethyl acetate (3×100 mL). The organic phase is dried and concentrated to provide 2-(4-acetylphenoxy)propanoic acid (5.0 g) (yield 92%): m.p. 104.3° C., IR (KBr) 3000 (br, vs), 2940 (br,s), 1754 (vs), 1650 (vs); $^1$H NMR (CDCl$_3$) delta 1.69 (d, J=6.8 Hz, 3H), 2.55 (s, 3H), 4.8 (q, J=6.8 Hz, 1H), 6.92 and 7.93 (dd, J=9.0 Hz, 4H).

EXAMPLE 7

A solution of 2-(4-acetylphenoxy)propionic acid (1.5 g, 7.2 mmol), hydroxylamine sulfate (0.72 g, 4.4 mmol), and concentrated sulfuric acid (2 drops) in acetic acid (30 mL) is refluxed for 4.25 hours. The reaction is quenched with sodium carbonate (0.25 g, 2.4 mmol) and concentrated to give a residue. The reaction residue is dissolved in water (50 mL) and extracted with ethyl acetate (2×100 mL). The ethyl acetate extract is dried and concentrated to give 2-(4-acetamidophenoxy)propionic acid (1.53 g) (yield 95%): m.p. 170°–172° C.; IR (KBr) 3400 (vs), 2900 (s) 1730 (vs), 1630 (vs), and 1603 (vs); $^1$H NMR (DMSO-d$_6$) delta 1.47 (d, J=6.8 Hz, 3H), 1.87 (s,3H), 2.06 (s,3H), 4.65 (q, J=6.8 Hz, 1H), 6.73 and 7.42 (dd, J=9.0 Hz, 4H).

EXAMPLE 8

To a solution of 2-(4-acetamidophenoxy)propionic acid (0.5 g, 2.2 mmol) in ethanol (10 mL) is added a drop of concentrated sulfuric acid and refluxed for 4 hours. The reaction is concentrated to dryness to give a residue. The residue is partitioned between water and ethyl acetate. The ethyl acetate layer is collected, dried (MgSO$_4$), and concentrated to give ethyl 2-(4-acetamidophenoxy)propanoate (0.44 g) (yield 80%): $^1$H NMR (CDCL$_3$) delta 1.27 (t, J=7.0 Hz, 3H), 1.60 (d, J=7.0 Hz, 3H), 4.25 (q, J=7.0 Hz, 2H), 4.76 (q, J=7.0 Hz, 1H), 6.84 and 7.46 (dd, J=9.0 Hz, 4H), and 8.02 (s, 1H).

EXAMPLE 9

Ethyl 2-(4-acetamidophenoxy)propanoate (5.0 g, 2.0 mmol) is hydrolyzed by refluxing for 6 hours at 80° C. with ethanol (10 mL) and 3 drops of concentrated hydrochloric acid. The reaction is concentrated under reduced pressure to obtain ethyl 2-(4-aminophenoxy)-propanoate (0.4 g) (yield 95%).

What is claimed is:

1. A method for synthesizing 2-(4-amidophenoxy)alkanoic acids or esters which comprises reacting a hydroxyaromatic ketone or benzaldehyde derivative of the formula

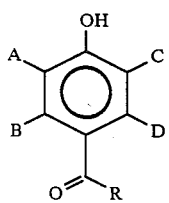

or a salt thereof; with a substituted acid or ester of the formula

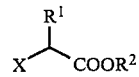

under basic conditions to thereby form a 2-(4-acylphenoxy)alkanoic acid or ester derivative of the formula

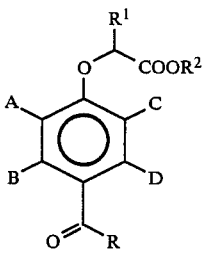

and then reacting this intermediate with H$_2$N—R$_3$ to form a 2-(4-acyliminophenoxy)alkanoic acid or ester of the formula

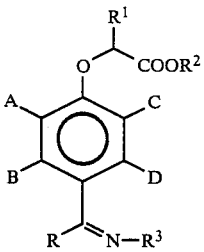

which is then subjected to a Beckmann Rearrangement in the presence of a catalyst to obtain a 2-(4-amidophenoxy)alkanoic acid or ester of the formula

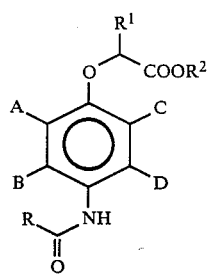

wherein R, R$^1$, R$^2$ and R$^4$ are independently H, C$_1$ to C$_{18}$ alkyl or C$_6$ to C$_{10}$ aryl; and R$^3$ is OH, O—SO$_3$H; and A, B, C and D are independently H, X, CF$_3$, NO$_2$, CN, C$_1$ to C$_4$ alkyl or alkoxy, or C$_6$ to C$_{10}$ aryl; and X is F, Cl, Br, I or a sulfonic ester.

2. The method of claim 1 wherein A, B, C and D are hydrogen.

3. The method of claim 1 wherein R is H.

4. The method of claim 1 wherein R is CH$_3$.

5. The method of claim 1 wherein the first reaction is conducted with a hydroxyaromatic ketone.

6. The method of claim 5 wherein said hydroxyaromatic ketone is 4-hydroxyacetophenone.

7. The method of claim 6 wherein said 4-hydroxyacetophenone is a potassium or sodium salt.

8. The method of claim 1 wherein R$^1$ is CH$_3$.

9. The method of claim 1 wherein R$^2$ is H.

10. The method of claim 1 wherein $R^2$ is alkyl.

11. The method of claim 1 wherein $R^2$ is $CH_3$, $C_2H_5$ or $C_4H_9$.

12. The method of claim 1, wherein said X-substituted acid or ester is optically active.

13. The method of claim 1 wherein X is bromine, chlorine, mesylate or tosylate.

14. The method of claim 1 wherein R is $CH_3$, $R^1$ is $CH_3$, $R^2$ is H, $CH_3$, $C_2H_5$ or $C_4H_9$ and X is bromine.

15. The method of claim 1 wherein said base is selected from the groups consisting of alkali metal and alkaline earth metal hydroxides or carbonates, amines and hydrides.

16. The method of claim 1 wherein said Beckmann Rearrangement is conducted with sulfuric acid as a catalyst.

17. The method of claim 16 wherein A, B, C and D are hydrogen, R is methyl, $R^2$ is H, methyl or ethyl, X is chlorine, bromine, mesylate or tosylate and said amine is hydroxylamine.

18. A method for synthesizing 2-(4-aminophenoxy)alkanoic acids or esters which comprises reacting a hydroxyaromatic ketone or benzaldehyde derivative of the formula

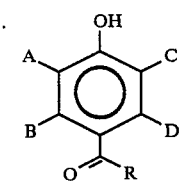

or a salt thereof; with a substituted acid or ester of the formula

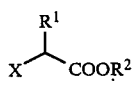

under basic conditions to thereby form a 2-(4-acylphenoxy)alkanoic acid or ester derivative of the formula

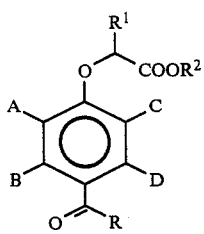

and then reacting this intermediate with $H_2N-R_3$ to form a 2-(4-acyliminophenoxy)alkanoic acid or ester of the formula

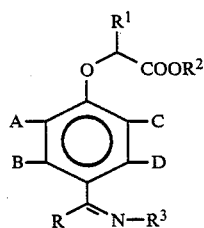

which is then subjected to a Beckmann Rearrangement in the presence of a catalyst to obtain a 2-(4-amidophenoxy)alkanoic acid or ester of the formula

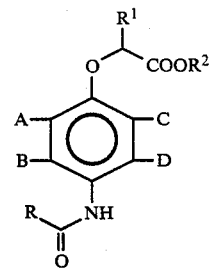

and then hydrolyzing or alcoholizing the 2-(4-amidophenoxy)alkanoic acid or ester with $R^4OH/H^+$ to obtain 2-(4-aminophenoxy)alkanoic acids and esters of the formula:

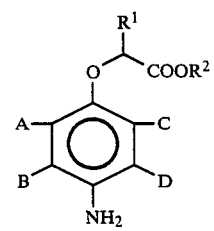

wherein R, $R^1$, $R^2$ and $R^4$ are independently H, $C_1$ to $C_{18}$ alkyl or $C_6$ to $C_{10}$ aryl; and $R^3$ is OH, O—$SO_3H$; and A, B, C and D are independently H, X, $CF_3$, $NO_2$, CN, $C_1$ to $C_4$ alkyl or alkoxy, or $C_6$ to $C_{10}$ aryl; and X is F, Cl, Br, I or a sulfonic ester.

19. The method of claim 18 wherein A, B, C and D are hydrogen.

20. The method of claim 18 wherein R is H.

21. The method of claim 18 wherein R is $CH_3$.

22. The method of claim 18 wherein the first reaction is conducted with a hydroxyaromatic ketone.

23. The method of claim 22 wherein said hydroxyaromatic ketone is 4-hydroxyacetophenone.

24. The method of claim 23 wherein said 4-hydroxyacetophenone is a potassium or sodium salt.

25. The method of claim 18 wherein $R^1$ is $CH_3$.

26. The method of claim 18 wherein $R^2$ is H.

27. The method of claim 18 wherein $R^2$ is alkyl.

28. The method of claim 18 wherein $R^2$ is $CH_3$, $C_2H_5$ or $C_4H_9$.

29. The method of claim 18 wherein X is bromine, chlorine, mesylate or tosylate.

30. The method of claim 18 wherein R is $CH_3$, $R^1$ is $CH_3$, $R^2$ is $CH_3$ and X is bromine.

31. The method of claim 18 wherein said base is selected from the groups consisting of alkali metal and alkaline earth metal hydroxides or carbonates, or hydrides.

32. The method of claim 18 wherein said Beckmann Rearrangement is conducted with sulfuric acid as a catalyst.

33. The method of claim 32 wherein A, B, C and D are hydrogen, R is methyl, $R^2$ is H, $CH_3$, $C_2H_5$, or $C_4H_9$, X is chlorine, bromine, mesylate ot tosylate and said amine is hydroxylamine.

34. The method of claim 18 wherein said alcoholysis is conducted with an alcohol, an ion exchange resin or an acid.

35. The method of claim 34 wherein said alcoholysis is conducted with hydrochloric acid.

36. The method of claim 18 wherein said X-substituted acid or ester is optically active.

* * * * *

UNITED STATES PATENT AND TRADEMARK OFFICE
CERTIFICATE OF CORRECTION

PATENT NO. : 4,883,901

DATED : 11-28-89

INVENTOR(S) : Varadaraj Elango

It is certified that error appears in the above-identified patent and that said Letters Patent is hereby corrected as shown below:

On the title page, item [75]:
Inventors name should read Varadaraj Elango.

Column 1, line 24, pages 1171-1178, should read pages 1171-1175,

Column 2, line 12, delete "b" in "2-(b4-acylphenoxy) alkanoic.

Column 2, line 13, delete "an".

Column 2, lines 30-43 (formula structure) should read as follows:

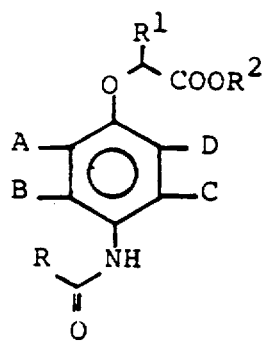

UNITED STATES PATENT AND TRADEMARK OFFICE
CERTIFICATE OF CORRECTION

PATENT NO. : 4,883,901

DATED : 11-28-89

INVENTOR(S) : Varadaraj Elango

It is certified that error appears in the above-identified patent and that said Letters Patent is hereby corrected as shown below:

Column 2, line 66, delete "S,O,N,"

Column 3, line 2 "oxidation" should read "oximation".

Column 3, line 20, add ")" after letter y in 2-(4-aminophenoxyalkanoic.

Column 5, line 64, "as" should read "at".

Column 6, line 21, "32" should read "=".

Column 6, line 26, insert "(" before "methylsulfonyl)

Column 7, line 39, "(CDCL3)" should read "(CDCl$_3$)".

Signed and Sealed this

Eleventh Day of June, 1991

*Attest:*

HARRY F. MANBECK, JR.

*Attesting Officer*  *Commissioner of Patents and Trademarks*